United States Patent [19]

Ishii et al.

[11] Patent Number: 5,178,662
[45] Date of Patent: Jan. 12, 1993

[54] BENZALDEHYDE ACETAL COMPOUNDS, PREPARATION PROCESS THEREOF, AND HERBICIDAL COMPOSITIONS CONTAINING THE SAME AS ACTIVE INGREDIENTS

[75] Inventors: Tsutomu Ishii; Katsutoshi Ishikawa; Sunao Maeda, all of Mobara; Masatoshi Gohbara, Tokyo; Yasunaga Iwasaki, Mobara; Makoto Nishida, Mobara; Sadafumi Koda, Mobara all of Japan

[73] Assignee: Mitsui Toatsu Chemicals, Inc., Tokyo, Japan

[21] Appl. No.: 807,129

[22] Filed: Dec. 16, 1991

[30] Foreign Application Priority Data

Dec. 17, 1990 [JP] Japan .................................. 2-402594

[51] Int. Cl.$^5$ .................. A01N 43/54; C07D 239/60
[52] U.S. Cl. .................... 504/243; 544/302; 504/178
[58] Field of Search .................. 544/302; 71/92

[56] References Cited

U.S. PATENT DOCUMENTS

| | | | |
|---|---|---|---|
| 4,770,691 | 9/1988 | Nezu et al. | 71/92 |
| 4,889,552 | 12/1989 | Wada et al. | 544/302 |
| 4,900,352 | 2/1990 | Wada et al. | 544/302 |
| 4,985,066 | 1/1991 | Wada et al. | 544/302 |
| 5,085,686 | 2/1992 | Vogelbacher et al. | 544/302 |

FOREIGN PATENT DOCUMENTS 62-258467 10/1988 Japan .
3-052873 7/1991 Japan .................................. 544/302

OTHER PUBLICATIONS

March, Advanced Org. Chem. 3rd Edition, pp. 789–791 (1985).

*Primary Examiner*—Cecilia Tsang
*Attorney, Agent, or Firm*—Millen, White, Zelano and Branigan, etc.

[57] ABSTRACT

Benzaldehyde acetal compounds represented by the following formula:

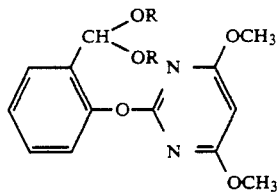

in which each R is a $C_{3-8}$ alkyl group and forms an ether bond with the corresponding oxygen atom of the orthoaldehyde moiety have no injury to crops and, moreover, exhibits superb herbicidal effects owing to the limitation of the number of carbon atoms of each alkyl group to 3–8.

18 Claims, No Drawings

BENZALDEHYDE ACETAL COMPOUNDS, PREPARATION PROCESS THEREOF, AND HERBICIDAL COMPOSITIONS CONTAINING THE SAME AS ACTIVE INGREDIENTS

BACKGROUND OF THE INVENTION (1) Field of the Invention

The present invention relates to novel benzaldehyde acetal compounds, a process for the preparation thereof, and herbicidal compositions containing one or more of the compounds as an active ingredient.

(2) Description of the Related Art

Pyrimidine derivatives having a phenoxy group at the 2-position are known to possess herbicidal activities as disclosed, for example, in Japanese Patent Laid-Open No. 258467/1988 as well as U.S. Pat. Nos. 4,985,066 and 4,770,971.

2-(4,6-Dimethoxypyrimidin-2-yloxy)-3-chlorobenzaldehyde dimethylacetal and 2-(4,6-dimethoxypyrimidin-2-yloxy)-3,5-dichlorobenzaldehyde dimethylacetal are exemplified in U.S. Pat. No. 4,985,066.

However, these dimethylacetals are not fully effective against weeds and, moreover, cause severe injury on crops. They are hence impractical.

SUMMARY OF THE INVENTION

An object of the present invention is to provide a compound which can exhibit excellent herbicidal effects against weeds without injury to crops.

The present inventors have proceeded with an extensive investigation with a view toward attaining the above object. As a result, it has been found that benzaldehyde acetal compounds having a $C_{3-8}$ alkyl group show reduced injury to crops such as soybean and cotton, exhibit a characteristic herbicidal spectrum centering around johnsongrass, shattercane, barnyardgrass (*Echinochloa crusgalli*), crabgrass (*Digitaria adsoendens*), *Imperata cylindrica* and Amaranth (*Amaranthus viridis*), and have excellent control effects against johnsongrass emerging from rhizome formed therein, leading to the completion of this invention.

The benzaldehyde acetal compounds of the present invention are represented by the following formula (I):

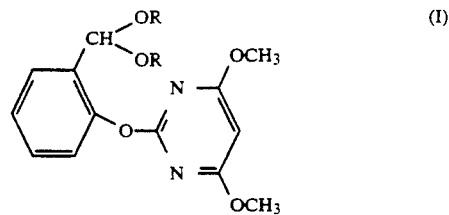

wherein R represents a linear or branched $C_{3-8}$ alkyl group.

Dimethyl- or diethylacetal compounds cause severe crop injury and, moreover, their herbicidal effects against weeds are insufficient. It has, however, been found that the acetal compounds represented by the formula (I) and containing $C_{3-8}$ alkyl groups have such low crop phytotoxicity as to not cause problem in practice and, moreover, have sufficient herbicidal effects against weeds. Their herbicidal effects against weeds show a characteristic spectrum. In particular, it is to be noted that they show extremely good effects against gramineous weeds - such as johnsongrass, shattercane and Imperara cylindrica - especially johnsongrass emerging from rhizome compared to conventional herbicides.

Herbicidal compositions containing one or more of the compounds of (I) have practically trouble-free phytotoxicity to crops such as soybean and cotton, show excellent control effects against johnsongrass with rhizome formed therein, said johnsongrass being said to be hardly controllable, by known herbicides and have the characteristic spectrum centering around shattercane, barnyardgrass (*Echinochloa crusgalli*), crabgrass (*Digitaria adscendens*), *Imperata cylindrica* Amaranth (*Amaranthus viridis*). Further, the herbicidal compositions according to this invention can show performance surpassing comparative chemicals such as the known compounds disclosed in the publications referred to above and other known compounds and are extremely useful herbicides.

DETAILED DESCRIPTION OF THE INVENTION AND PREFERRED EMBODIMENTS

The benzaldehyde acetal compounds represented by formula (I) are characterized in that each alkyl group forming an ether bond with its corresponding oxygen atom in the orthoaldehyde moiety has 3-8 carbon atoms and, owing to this characteristic feature, they have significantly reduced phytotoxicity to crops and excellent herbicidal effects against weeds.

Compounds of the present invention can be prepared according to the following reaction scheme:

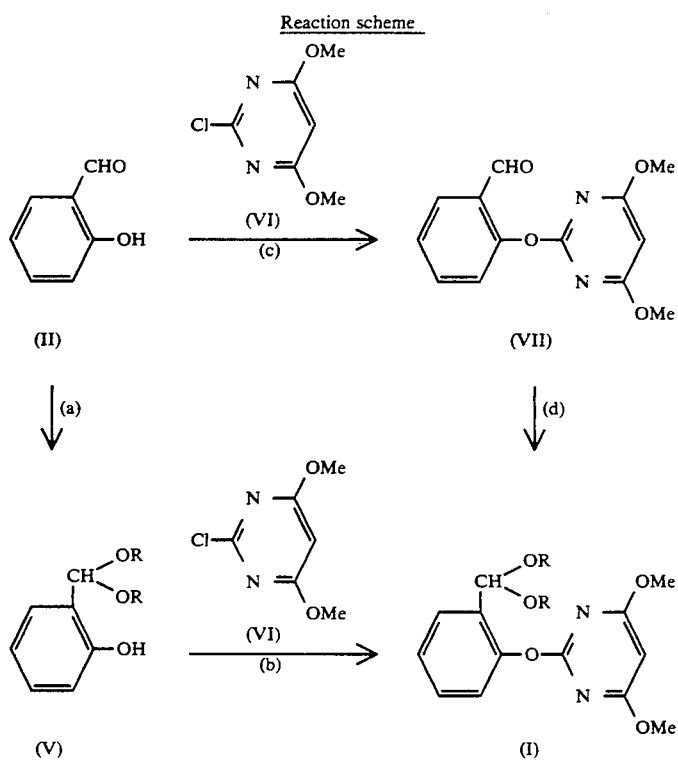

Reaction scheme

The steps (b) and (c) are carried out under exactly the same conditions. Namely, the compound (VII) can be prepared by heating 2-hydroxybenzaldehyde represented by the formula (II) and 2-chloro-4,6-dimethoxypyrimidine represented by the formula (VI) in an inert solvent, in the presence of a base, within the temperature range of from 50° C. to the boiling point of the solvent, for 1-10 hours. Illustrative of the base include alkali metals such a metallic sodium and metallic potassium; alkali metal hydroxides such as sodium hydroxide and potassium hydroxide; and alkali metal carbonates such as sodium carbonate and potassium carbonate.

Exemplary solvents include aromatic hydrocarbons such as benzene, toluene and xylene; ethers such as tetrahydrofuran, dioxane and diglyme; ketones such as acetone and methyl ethyl ketone; aprotonic polar solvents such as dimethylformamide, dimethylacetamide, dimethylimidazolidinone and dimethylsulfoxide; acetonitrile; and water.

The steps (a) and (d) can be conducted according to the method described in Japanese Patent Laid-Open No. 13534/1983. In general, processes for converting an aldehyde group to an acetal group can be applied. These processes will next be described specifically.

(1) Process in which an alcohol is reacted in the presence of an acid catalyst:

A corresponding alcohol is reacted in the presence of an acid. The alcohol can be used in an amount ranging from its stoichiometric amount to a large excess, the latter including the portion employed as a solvent. When an alcohol is used in a stoichiometric amount, a solvent inert to the reaction can be used. Illustrative of the solvent are aromatic hydrocarbons such as benzene, toluene and xylene; ethers such as tetrahydrofuran, dioxane and diglyme; aprotonic polar solvents such as dimethylformamide, dimethylacetamide, dime- thylimidazolidinone dimethylsulfoxide; and acetonitrile.

Illustrative of the acid are mineral acids such as hydrochloric acid and sulfuric acid; and organic sulfonic acids such as methanesulfonic acid, benzenesulfonic acid and p-toluenesulfonic acid. The reaction temperature may range from 0° C. to the boiling point of the solvent used. It is however desirable to conduct the reaction within the range of from 20° C. to the boiling point. The reaction can generally be brought to completion in 1-10 hours although the reaction time varies depending on the reaction temperature.

(2) Process in which an orthoformate ester is reacted:

An acetal can also be obtained easily by reacting a corresponding orthoformate ester. The orthoformate ester can be used in an excess amount including a portion employed as a solvent, or the corresponding alcohol can be employed as a solvent. Other solvent inert to the reaction may also be used in some instances. In many cases, the reaction tends to smoothly proceed by the addition of a weakly acidic substance such as ammonium chloride as a catalyst. It is desirable to conduct the reaction at a temperature of from 50° C. to the boiling point, although the reaction temperature may range from 0° C. to the boiling point. The reaction is generally brought to completion in 2-8 hours.

Herbicidal compositions of the invention, which contain one or more of the benzaldehyde acetal compounds represented by formula (1), act extremely effectively against most harmful weeds which cause problems in paddy fields or upland fields. In paddy fields, they show extremely good herbicidal effects against very troublesome gramineous weeds such as barnyardgrass, *Leersia oryzoides* and common reed; very troublesome cyperaceous weeds such as *Cyperus microiria*, smallflower umbrellaplant, *Cyperus seroyinus*, bulrush, *Scirpus nipponicus*, *Eleocharis kuroguwai*, Needle spikerush and

*Fimbristylis miliacea*; very troublesome arrowhead weeds such as *Sagittaria pygmaea*, arrowhead and *Alisma canalicularum*; and broadleaf weeds such as *Monochoria vaginalis*, toothcup and *Oenanthe javanica*. In upland fields, they exhibit superb herbicidal effects against broadleaf weeds such as common chickweed, common lambsquarters, shepherd's purse, amaranth, hemp sesbania and velvetleaf; gramineous weeds such as barnyardgrass, green foxtail, large crabgrass, goosegrass, annual bluegrass, blackgrass, oat, wild oat, quackammonium grass, downy brome, bermudagrass, creeping bentgrass, broomsedge, silky bentgrass, fall panicum, johnsongrass, shattercane and woolly cupgrass; cyperaceous weeds such as rice flatsedge; especially perennial intractable weeds such as johnsongrass, shattercane and orchardgrass.

In an enzyme-level inhibitory activity test on ALS (acetolactate syntase), which is believed to be a target site by the compounds of the invention represented by formula (1), the herbicidal compositions containing one or more of the compounds of the invention have been found to show high inhibitory activities against weeds such as barnyardgrass, johnsongrass and green foxtail, as will be understood from the results of the test to be described later under Test 1. In contrast, they do not show inhibitory activities against broadleaf crops such as pea, cotton and peanut. These results indicate that pea, cotton, peanut and the like show high tolerance against the herbicidal compositions according to the invention. In pot tests, they were also found to show no injury or extremely slight injury against crops such as corn, soybean, cotton, beet, peanut, common sunflower, rape, potato and greens. Depending on the method of application, they can also be used, without any injury, for gramineous crops such as wheat, rice, barley and sugar cane. It is however to be noted that use of the herbicidal compositions of the invention is not limited to these crops.

The herbicidal compositions containing one or more of the compounds of the invention, which are represented by formula (1), are effective in all application methods such as soil application, soil incorporation, foliar application and band application. They can be used at an application rate in the wide range of from 0.01 kg/ha to 10 kg/ha in terms of active ingredient. As a standard, it is however preferred to use them at an application rate of from 0.1 kg/ha to 5 kg/ha.

Upon application of the compounds of the formula (1) according to this invention as herbicides, they may be applied neat to weeds to be treated. In general, they are however mixed with an inert liquid carrier or solid carrier and are formed into a commonly-used formulation such as powder, granules, wettable powder, emulsion or flowable formulation. One or more auxiliary agents can also be added if necessary for formulation.

Any carrier can be used as long as it is usable in conventional agricultural or horticultural chemicals, no matter whether it is solid or liquid. No particular limitation is therefore imposed on the carrier.

Exemplary solid carriers include mineral powders such as clay, talc, bentonite, calcium carbonate, diatomaceous earth and white carbon; vegetable powders such as soybean flour and starch; high molecular compounds such as petroleum resins, polyvinyl alcohol and polyalkylene glycols; urea; and waxes. Illustrative liquid carriers include various organic solvents such as xylene, methylnaphthalene and alkylbenzenes; various oils such as vegetable oils; and water.

As auxiliary agents, surfactants, binders (e.g., lignine sulfonic acid, alginic acid, polyvinyl alcohol, gum arabic, sodium CMC), stabilizers (e.g., phenol compounds, thiol compounds and higher fatty acid esters for the prevention of oxidation; phosphate salts as pH regulators; and in some instances, light stabilizers), and the like—which are generally used in agricultural or horticultural chemicals—can be used either singly or in combination. In some instances, industrial fungicides, antiseptics and the like can also be incorporated for the control of bacteria and fungi.

As exemplary surfactants, non-ionic, anionic, cationic and amphoteric surfactants can be used either singly or in combination as needed. Those obtained by adding ethylene oxide (for example, "X-77", trade name; or "Neugen EA80", trade name) or propylene oxide to alkylphenols, higher alcohols, alkylnaphthols, higher fatty acids, fatty acid esters and the like can be used as preferred non-ionic surfactants. Preferred exemplary anionic surfactants include the alkylsulfonate salts (e.g., "Neopelex", trade name), alkylsulfate ester salts, phosphate ester salts and the like of alkylphenols, alkylnaphthols, higher alcohols, higher fatty acids, fatty acid esters and the like. Lignin-sulfonate salts (e.g., "Sunekis", trademark) are also preferred examples.

The content of each compound of formula (I) in the associated herbicidal composition according to the invention varies depending on the formulation. In general, it can be 0.05-20 wt.% in a powder, 1-50 wt.% in a wettable powder, 0.05-15 wt.% in a granule, 1-50 wt.% in an emulsion, 1-50 wt.% in a flowable formulation and 1-50 wt.% in a dry flowable formulation. Preferably, it can be 0.5-5 wt.% in a powder, 10-40 wt.% in a wettable powder, 0.5-8 wt.% in a granule, 5-20 wt.% in an emulsion, 10-30 wt.% in a flowable formulation and 10-40 wt.% in a dry flowable formulation.

The total content of auxiliary agents may be 0-80 wt.%. The content of the carrier is the value which is obtained by subtracting the contents of the compound as an active ingredient and of auxiliary agents from 100 wt.%.

The herbicidal compositions of the invention, which contain one or more of the compounds represented by the formula (I), may be formulated together with one or more other herbicides or with one or more of agricultural chemicals such as fungicides, insecticides and plant growth regulators, fertilizers and soil improving agents, to say nothing of combined use therewith. Synergistic effects may be expected in some instances.

The term "other herbicides" as used herein can mean the following compounds as active ingredient, although not necessarily limited thereto:
3,6-Dichloro-2-methoxybenzoic acid (dicamba)
2,5-Dichloro-3-aminobenzoic acid (amiben)
4-Chloro-2,2-dimethylvaleranilide (monalide)
3,4-Dichloropropionanilide (propanil)
3,4-Dichloro-2-methylacrylanilide (dicryl)
3,4-Dichlorocyclopropanecarboxanilide (crypromid)
3,4-Dichloro-2-methyl-pentananilide (karsil)
N,N-Dimethyl-2,2-diphenylacetamide (diphenamide)
N-naphthylphthalamic acid (naptalam)
N-(1,1-Dimethylbenzyl)-2-bromo-tert-butylacetamide (buromobutide)
2-Benzothiazol-2-yloxy-N-methylacetanilide (mefenasate)
1,1-Dimethyl-3-phenylurea (fenuron)
3-(4-Chlorophenyl)-1,1-dimethylurea (monuron)

3-(4-Chlorophenyl)-1-methoxy-1-methylurea (monolinuron)
1-(2-Methylcyclohexyl)-3-phenylurea (siduron)
1,1-Dimethyl-3-(3-trifluoromethylphenyl)urea (fluometuron)
3-(3,4-Dichlorophenyl)-1,1-dimethylurea (diuron)
3-(3,4-Dichlorophenyl)-1-methoxy-1-methylurea (linuron)
3-(3-Chloro-4-methylphenyl)-1,1-dimethylurea (chlortoluron)
3-[3-(N-Tert-butylcarbamoyloxy)phenyl]-1,1-dimethylurea (karbutilate)
1-(α,α-Dimethylbenzyl)-3-(4-methylphenyl)urea (dymron)
3-(4-Isopropylphenyl)-1,1-dimethylurea (isoproturon)
3-(2-Benzothiazolyl)-1,3-dimethylurea (methabenzthiazuron)
3-(2-Benzothiazolyl)-1-methylurea (benzthiazuron)
3-(Hexahydro-4,7-methanoindan-5-yl)-1,1-dimethylurea (noruron)
3-[5-(1,1-Diemthylethyl)-1,3,4-thiadiazol-2-yl]-1,3-dimethylurea (tebuthiuron)
3-(5-Tert-butylisooxazol-3-yl)-1,1-dimethylurea (isouron)
2-Chloro-4,6-bis(ethylamino)-1,3,5-triazine (simazine)
2-Chloro-4-ethylamino-6-isopropylamino-1,3,5-triazine (atrazine)
2-Chloro-4,6-bis(isopropylamino)-1,3,5-triazine (propazine)
2-(2-Chloro-4-ethylamino 1,3,5-triazin-6-yl-amino)-2-methylpropionitrile (cyanazine)
2-Methoxy-4,6-bis(isopropylamino)-1,3,5-triazine (prometon)
2-Methylthio-4,6-bis(ethylamino)-1,3,5-triazine (simetryne)
2-Methylthio-4,6-bis(isopropylamino)-1,3,5triazine (prometryne)
2-Methylthio-4-isopropylamino-6-methylamino-1,3,5-triazine (ametryne
2-Methylthio-4-isopropylamino-6-methylamino-1,3,5-triazine (desmetryne)
4-Amino-6-tert-butyl-3-methylthio-1,2,4-triazin-5(4H)-one (metribuzin)
3-Cyclohexyl-6-dimethylamino-1-methyl-1,3,5-triazin-2,4-(1H,3H)-dione (hexazinone)
2-Chloro-N-isopropylacetanilide (propachlor)
N-Methoxymethymethyl-2′,6′-diethyl-2-chloroacetanilide (alachlor)
2-Chloro-2′,6′-diethyl-N-(butoxymethyl)acetanilide (butachlor)
2-Chloro-2′-ethyl-6′-methyl-N-(2-methoxy-1-methylethyl)acetanilide (metolachlor)
N,N-Diallyl-2-chloroacetamide (allidochlor)
2,6-Dinitro-N,N-dipropyl-4-trifluoromethylaniline (trifluralin)
3,4-Dimethyl-2,6-dinitro-N-1-ethylpropylaniline (pendimethalin)
2-Chloro-N-(4-methoxy-6-methyl-1,3,5-triazin-2-ylaminocarbonyl)benzenesulfonamide (chlorosulfuron)
Methyl 2-[3-(4-methoxy-6-methyl-1,3,5-triazin-2-yl)ureidosulfonyl]benzoate (metsulfurone-methyl)
Methyl 2-[3-(4,6-dimethylpyrimidin-2-yl)ureidosulfonyl]benzoate (sulfometuron-methyl)
Methyl 2-[3-(4,6-dimethoxypyrimidin-2-yl)ureidosulfonyl]benzoate (bensulfuron)
Ethyl 2-[3-(4-chloro-6-methoxypyrimidin-2-yl)ureidosulfonyl]benzoate (chlorinuron)
3-[(4-Methoxy-6-methyl-1,3,5-triazin-2-yl)ureidosulfonyl]-2-thiophenecarboxylic acid (thiameturon)
2-(4-Isopropyl-4-methyl-5-oxo-2-imidazolin-2-yl)-nicotinic acid isopropylamine salt (imazapyr)
2-(4-Isopropyl-4-methyl-5-oxo-2-imidazolin-2-yl)-3-quinolic acid (imazaquin)
2-(4-Isopropyl-4-methyl-5-oxo-2-imidazolin-2-yl)-5-ethyl-3-pyridinecarboxylic acid (imazethapyr)
Methyl 2-(4-isopropyl-4-methyl-5-oxo-2-midazolin-2-yl)-3(4)-benzoate (imadazolinone)
3-Isopropyl-1H-2,1,3-benzothiazin-4(3H)-one-2,2-dioxide (bentazon)
5-Bromo-3-sec-butyl-6-methyluracil (bromacil)
3,5-Dibromo-4-hydroxybenzonitrile (bromoxynil)
4-Hydroxy-3,5-diiodobenzonitrile (ioxynil)
N-(Phosphonomethyl)glycine (glyphosate)

Preparation of certain compounds according to the invention will next be described specifically by the following examples.

REFERENTIAL EXAMPLE 1

Synthesis of 2-(4,6-dimethoxypyrimidin-2-yloxy)-benzaldehyde (intermediate)

After 2.2 g of salicylaldehyde were dissolved in 100 ml of dimethylformamide, 4.0 g of 60% sodium hydride were added little by little. The resulting mixture was stirred at room temperature for a while and, after foaming subsided, 17.5 g of 2-chloro-4,6-dimethoxypyridine were added, followed by heating to 100° C. After the mixture was stirred for 3 hours at the same temperature, dimethylformamide was recovered under reduced pressure. The residue was isolated by column chromatography on a silica gel and then eluted with a 7:3 mixed solvent of n-hexane and ethyl acetate, whereby 14.8 g of the target compound, 2-(4,6-dimethoxypyrimidine-2-yloxy)benzaldehyde, were obtained as crystals (m.p.: 96°-98° C.; yield: 56.9%).

IR (KBr) cm$^{-1}$: 2720, 1710.

NMR (400 MHz, CDC;3) δ from TMS: 3.80(6H,s), 5.81(1H,s), 7.27(1H,m), 7.36(1H,m), 7.64(1H,m), 7.95(1H,m), 10.24(1H,s).

EXAMPLE 1

Synthesis of 2-(4,6-dimethoxypyrimidin-2-yloxy)benzaldehyde di-n-butylacetal (Compound No. 3)

2-(4,6-Dimethoxypyrimidin-2-yloxy)benzaldehyde obtained in Referential Example 1 (1.5 g), n-butyl orthoformate (1.6 g) and ammonium chloride (0.03 g) were added to 40 ml of n-butyl alcohol, followed by stirring under reflux. Two hours later, the reaction was terminated. The reaction mixture was concentrated under reduced pressure. The residue was subjected to chromatography on a silica gel column and then eluated with a 7:3 mixed solvent of n-hexane and ethyl acetate to purify the same, whereby 1.6 g of the target compound, 2-(4,6-dimethoxypyrimidin-2-yloxy)benzaldehyde di-n-butylacetal, were obtained (yield: 71.1%).

EXAMPLE 2

Synthesis of 2-(4,6-dimethoxypyrimidin-2-yloxy)benzaldehyde d-n-hexylacetal (Compound No. 5)

2-(4,6-Dimethoxypyrimidin-2-yloxy)benzaldehyde (1.5 g), n-hexyl orthoformate (2.7 g) and ammonium chloride (0.03 g) were added to 40 ml of n-hexyl alcohol, followed by stirring under reflux. Two hours later, the reaction was terminated. The reaction mixture was concentrated under reduced pressure. The residue was subjected to chromatography on a silica gel column and then eluated with a 7:3 mixed solvent of n-hexane and ethyl acetate to purify the same, whereby 1.7 g of the target compound, 2-(4,6-dimethoxypyrimidin-2-yloxy)-benzaldehyde di-n-hexylacetal, were obtained (yield: 66%).

EXAMPLE 3

Synthesis of 2-(4,6-dimethoxypyrimidin-2-yloxy)benzaldehyde di-n-octylacetal (Compound No. 7)

To a mixed solvent of 40 ml of n-octanol and 15 ml of benzene, 1 g of salicylaldehyde was added. The mixture was poured into an eggplant-type flask equipped with a SHEALAM cap, followed by purging with nitrogen. After the addition of 0.04 g of dichlorotris(triphenylphosphine)ruthenium, the mixture was reacted under heating at 100° C. for 20 hours. After the completion of the reaction, the reaction mixture was filtered and the filtrate was concentrated under reduced pressure. The residue thus obtained (0.9 g) was dissolved in 10 ml of DMF, followed by the addition of 0.5 g of 2-chloro-4,6-dimethoxypyrimidine and 0.2 g of potassium carbonate. The resulting mixture was reacted under heating at 110° C. for 3 hours. After the completion of the reaction, the reaction mixture was poured into 100 ml of water, followed by extraction three times, with 50 ml each of ethyl acetate. The organic layer was washed, dried and concentrated under reduced pressure. The residue was subjected to chromatography on a silica gel column and then eluated with a 7:3 mixed solvent of n-hexane and ethyl acetate to purify the same, whereby 0.7 g of the target compound, 2-(4,6-dimethoxypyrimidin-2-yloxy)-benzaldehyde di-n-octylacetal, was obtained (yield 17%).

REFERENTIAL EXAMPLE 2

Synthesis of 2-(4,6-dimethoxypyrimidin-2-yloxy)benzaldehyde dimethylacetal (Comparative Compound C)

A mixture consisting of 52.6 g of 2-(4,6-dimethoxypyrimidin-2-yloxy)benzaldehyde, 42.9 g of methyl orthoformate, 0.48 g of ammonium chloride and 500 ml of methanol was reacted at the reflux point for 5 hours under stirring. After the reaction mixture was cooled to room temperature, the precipitate was filtered off. The filtrate was concentrated under reduced pressure. The residue was subjected to chromatography on a silica gel column and then eluated with a 7:3 mixed solvent of n-hexane and ethyl acetate to purify the same, whereby 61.0 g of the target compound, 2-(4,6-dimethoxypyrimidin-2-yloxy)benzaldehyde dimethylacetal, were obtained as an oil (yield: 98%).

NMR (400 MHz, CDCl$_3$) δ from TMS: 3.26(6H,s), 3.79(6H,s), 5.64(1H,s), 5.76(1H,s), 7.13(1H,d,J=8.1Hz), 7.23–7.27(1H,m), 7.34–7.38(1H,m), 7.64–7.66(1H,dd,J=8.1&1.5Hz)

REFERENTIAL EXAMPLE 3

Synthesis of 2-(4,6-dimethoxypyrimidin-2-yloxy)benzaldehyde diethylacetal (Comparative Compound D)

The target compound was synthesized as an oil in a similar manner to Referential Example 2 (yield: 90%).
NMR (400 MHz, CDCl$_3$) δ from TMS: 1.11(6H,t,J=7.3Hz), 3.51(4H,q,J=7.3Hz), 3.79(6H,s), 5.72(1H,s), 5.74(1H,s), 7.11(1H,d,J=8.1Hz), 7.22–7.26(1H,m), 7.32–7.36(1H,m), 7.67–7.69(1H,m)

Certain compounds were prepared in accordance with the procedures of Examples 1–3. They are summarized in Table 1.

TABLE 1

| Comp'd No. | R | form | NMR (400MHz) (CDCl$_3$:δ TMS) | Synthesis route |
|---|---|---|---|---|
| 1 | -n-C$_3$H$_7$ | oil | 0.85(6H, d, J=7.3Hz), 1.45–1.53(4H, m), 3.35–3.48(4H, m), 3.79(6H, s), 5.73(1H, s), 5.74(1H, s), 7.12(1H, d, J=8.1Hz), 7.22–7.25(1H, m), 7.31–7.35(1H, m), 7.68–7.70 (1H, dd, J=8.1 & 1.5Hz) | d |
| 2 | -i-C$_3$H$_7$ | oil | 1.00(6H, d, J=5.9Hz), 1.17(6H, d, J=5.9Hz), 3.84(6H, s), 4.12–4.18 (2H, m), 5.49(1H, s), 6.99(1H, s), 7.19–7.24 (2H, m), 7.33–7.39(2H, m) | d |
| 3 | -n-C$_4$H$_9$ | oil | 0.84–0.87(6H, t, J=7.3Hz), 1.24–1.34(4H, m), 1.41–1.51(4H, m), 3.37–3.52 (4H, m), 3.79(6H, s), 5.70(1H, s), 5.75(1H, s), 7.11(1H, d, J=8.1Hz), 7.22–7.27(1H, m), 7.31–7.35(1H, m), 7.66–7.68 (1H, m) | d |
| 4 | -n-C$_5$H$_{11}$ | oil | 0.83–0.87(6H, m), 1.21–1.31(8H, m), 1.43–1.50 (4H, m), 3.37–3.48(4H, m), 3.79(6H, s), 5.71(1H, s), 5.75(1H, s), 7.12(1H, d, J=8.0Hz), 7.24–7.26 (1H, m), 7.31–7.34(1H, m), 7.66–7.68(1H, m) | d |
| 5 | n-C$_6$H$_{13}$ | oil | 0.84–0.89(6H, m), 1.03–1.31(12H, m), 1.41–1.47 (4H, m), 3.37–3.49(4H, m), 3.78(6H, s), 5.71(1H, s), 5.74(1H, s), 7.11–7.12 (1H, m), 7.24–7.27(1H, m), 7.31–7.34(1H, m), 7.66–7.68(1H, m) | d |
| 6 | n-C$_7$H$_{15}$ | oil | 0.85–0.88(6H, m), 1.23–1.31(16H, m), 1.44–1.53 (4H, m), 3.39–3.48(4H, m), 3.79(6H, s), 5.71(1H, s), 5.74(1H, s), 7.12(1H, d, J=8.0Hz), 7.24–7.26 (1H, m), 7.31–7.34(1H, m), 7.66–7.68(1H, m) | d |
| 7 | n-C$_8$H$_{17}$ | oil | 0.85–0.89(6H, m), 1.23–1.30(20H, m), 1.42–1.47 (4H, m), 3.37–3.48(4H, m), 3.78(6H, s), 5.71(1H, s), 5.74(1H, s), 7.12(1H, d, J=8.0Hz), 7.22–7.26, (1H, m), 7.31–7.34(1H, m), 7.66–7.68(1H, m) | d |

Formulation examples and herbicidal activity tests of certain herbicidal compositions according to the invention will next be described.

FORMULATION EXAMPLE 1

Wettable powder

A wettable powder was obtained by thoroughly grinding and mixing 20 parts by weight of Compound No. 1 of the invention, 2 parts by weight of "Neopelex" (trade mark, product of Kao Corporation; sodium dodecyl benzene sulfonate), 1 part by weight of "Neugen EA80" (trade name, product of Sanyo Chemical Industries, Ltd.; polyoxyethylene nonylphenyl ether), 5 parts by weight of white carbon and 72 parts by weight of diatomaceous earth.

FORMULATION EXAMPLE 2

Wettable powder

A wettable powder was obtained by thoroughly grinding and mixing 20 parts by weight of Compound No. 2 of the invention, 2 parts by weight of sodium alkylbenzenesulfonate, 1 part by weight of polyoxyethylene alkylphenyl ether and 77 parts by weight of "Zeaklite".

FORMULATION EXAMPLE 3

Wettable powder

A wettable powder was obtained by thoroughly grinding and mixing in a Jet-O-Miser 50 parts by weight of Compound No. 3 of the invention, 5 parts by weight of white carbon, 6 parts by weight of ammonium polyoxyethylene alkylphenyl ether sulfate, 2 parts by weight of sodium ligninesulfonate and 37 parts by weight of diatomaceous earth.

FORMULATION EXAMPLE 4

Flowable formulation

A flowable formulation was obtained by adding 76.7 parts by weight of water to the mixture of 20 parts by weight of Compound No. 5 of the invention, 2 parts by weight of sodium ligninesulfonate, 0.3 part by weight of xanthan gum and 1 part by weight of polyoxyethylene alkylaryl ether, mixing them and then finely grinding the resultant mixture in a sand grinder.

FORMULATION EXAMPLE 5

Flowable Formulation

A flowable formulation obtained by wet grinding and mixing 30 parts by weight of Compound No. 2 of the invention and a solution of 10 parts by weight of "Sun Ekisu P252" (trade name, product of Sanyo-Kokusaku Pulp Co., Ltd.; sodium ligninesulfonate) in 50 parts by weight of water, adding 0.2 part by weight of "Deltop" (trade mark, product of Takeda Chemical Industries, Ltd.; organic iodine antiseptic) and a solution of 0.2 part by weight of "Kelzan S" (trade name, product of Kelco Corp.; xanthan gum) in 9.6 parts by weight of water and then mixing the resultant mixture.

FORMULATION EXAMPLE 6

Powder

A powder was obtained by thoroughly grinding and mixing 1 part by weight of Compound No. 1 of the invention, 0.5 part by weight of "Emulgen 910" (trade name, product of Kao Corporation; polyoxyethylene nonylphenyl ether) and 98.5 parts by weight of kaolin clay.

FORMULATION EXAMPLE 7

Powder

A powder was obtained by grinding and mixing 3 parts by weight of Compound No. 4 of the invention, 3 parts by weight of sodium ligninesulfonate, 2 parts by weight of polyoxyethylene alkylaryl ether and 92 parts by weight of clay.

FORMULATION EXAMPLE 8

Dry flowable formulation

A dry flowable formulation was obtained by mixing 60 parts by weight of Compound No. 6 of the invention, 5 parts by weight of sodium alkylbenzenesulfonate, and 35 parts by weight of polypropylene glycol polyethylene glycol ether.

FORMULATION EXAMPLE 9

Granules

One part by weight of Compound No. 3 of the invention, 2 parts by weight of "Neopelex" (trade mark; described above), 2 parts by weight of "Sun Ekisu P252" (trade name; described above), 70 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30°–60° C. in air and then crushed into granules, the granules were classified by a sifting machine to collect granules of 0.3–2 mm.

FORMULATION EXAMPLE 10

Granules

One part by weight of Compound No. 6 of the invention, which had been finely ground, 2 parts by weight of "Gosenol GL-05s" (trade name, product of The Nippon Synthetic Chemical Industry Co., Ltd.; PVA), 2 parts by weight of "Sun Ekisu P-252" (trade name; described above) and 95 parts by weight of clay were thoroughly mixed. A suitable amount of water was added to the resultant mixture to wet the same, followed by extrusion of the mass through a small injection molding machine into pellets. After the pellets were dried at 60°–90° C. in air and then crushed into granules, the granules wre classified by a sifting machien to collect granules of 0.3–1 mm.

FORMULATION EXAMPLE 11

Emulsion

Ten parts by weight of Compound No. 2 of the invention, 10 parts by weight of "Sorpole 800A" (trade name, product of Toho Chemical Industries Co., Ltd.; a nonionic/anionic surfactant mixture) and 80 parts by weight of o-xylene were mixed into an emulsion.

FORMULATION EXAMPLE 12

Emulsion

Ten parts by weight of Compound No. 3 of the invention, 10 parts by weight of "Sorpole 800A" (trade name; described above) and 80 parts by weight of o-xylene were mixed into an emulsion.

Test 1

ALS (Acetolactate Syntase) Inhibition Test

To determine the selectivity in enzyme level between crops and weeds, an ALS inhibition test was conducted using pea as a typical broadleaf crop and barnyardgrass as a representative gramineous weeds.

After seeds of pea and barnyardgrass were allowed to germinate at 25° C. for 8–14 days in a dark place, partially-purified suspensions (Suspensions A) of acetolactate syntase were separately obtained from the seedlings in accordance with the procedures described in the literature, Plant Physiology, 75, 827–831. In a test tube, 0.5 mg of one of test compounds was weighed, followed by the addition of 0.15 ml of a 20 mM $K_2HPO_4$ solution and 0.25 ml of a reaction substrate medium which consisted of 40 mM of $K_2HPO_4$, 40 mM of sodium pyruvate, 1 mM of TPP, 1 mM of $MgCl_2$ and 20 μM of FAD so that 0.4 ml of a reaction solution (Solution B) was prepared. Added to 0.4 ml of Solution B was 0.1 ml of Suspension A. After the resultant mixture was shaken for 1 hour in a thermostat water bath controlled at 30° C., 50 μl of 6N sulfuric acid were added to terminate the reaction.

Next, the test tube with the reaction-terminated liquid mixture contained therein was transferred into a thermostat water bath controlled at 60° C. and was heated for 15 minutes. Thereafter, 0.5 ml of a 0.5% creatine solution and 0.5 ml of a 5% alkaline α-naphthol solution were added, and the resultant mixture was maintained at 60° C. for 15 minutes. As a result, the test solution developed a pink-to-red color. After the above operation, the absorbance of the test solution at 525 nm was measured by a spectrophotometer (Absorbance ① of Test Compound).

Further, the absorbance (Absorbance ② of Blank) of a solution obtained by subjecting a portion of Solution B to the above procedures without addition of any test compound and the absorbance (Absorbance ③ of sulfuric acid) of another solution obtained by subjecting another portion of Solution B to the above procedures which using 50 μl of 6N sulfuric acid as a test compound were also measured. Based on the respective measurement values, the enzymoreaction inhibition rate at 10,000 ppm (0.5 μg/0.5 ml) of each compound was determined in accordance with the below-described formula. The results are shown in Table 2.

Incidentally, the following compounds were used as Comparative Compounds A and B (this also applies to Test 2 and Test 3).

TABLE 2

| Compound | Enzymoreaction inhibition rate (%) | |
|---|---|---|
| | Barnyardgrass | Pea |
| Compound No. 1 | 100 | 0 |
| Compound No. 2 | 100 | 0 |
| Compound No. 3 | 100 | 0 |
| Compound No. 4 | 100 | 0 |
| Compound No. 5 | 100 | 0 |
| Compound No. 6 | 100 | 0 |
| Compound No. 7 | 100 | 0 |
| Comp. Comp'd A | 73 | 72 |
| Comp. Comp'd B | 98 | 92 |

A: [structure with COOCH₃ and OCH₃ groups]

B: [structure with CHO and OCH₃ groups]

(Compounds A and B are both disclosed in Japanese Patent Laid-Open No. 174059/1987)

$$\text{Enzymoreaction inhibition rate} = \left(1 - \frac{①-③}{②-③}\right) \times 100$$

The results of the test indicate that the compounds of the invention show strong inhibition in enzyme level against gramineous weeds such as barnyardgrass but show no inhibition to broadleaf crops such as pea, in other words, have distinct selectivity.

Test 2

Upland Soil Application Test

Resin-made 1/1000-are pots were filled with the soil of an upland field. After they were fertilized, cotton and soybean were seeded and 3 cm soil covering was applied. In addition, amaranth, common lambs-quarters, barnyardgrass, green foxtail, large crabgrass and johnsongrass were seeded and 1 cm soil covering was applied. One day later, a wettable powder prepared from a predetermined amount of each test compound in a similar manner to the procedures described in Formulation Example 1 was diluted with water and then sprayed evenly at an application rate equal to 10 l per are onto the surface of the soil by means of a pressure-operated sprayer. The weeds and crops were allowed to grow in a green house and influence to them were observed on the 50th day after the spray. The results are shown in Table 3. The degree of damages of each test plant and the degree of injury to each crop were determined by measuring fresh weight in each group and indicated by % calculated according to the following formula.

$$\text{Herbicidal effect (\%) (degree of injury to crop)} = \frac{\text{Fresh weight in untreated group} - \text{Fresh weight in treated group}}{\text{Fresh weight in untreated group}} \times 100$$

TABLE 3

| | Results of Upland Soil Treatment Test | | | | | | | |
|---|---|---|---|---|---|---|---|---|
| | | Herbicidal effects | | | | | Crop injury | |
| Application rate of active ingredient (g ai/a) | Amaranth (*Amaranthus viridis*) | Common lambs-quarters | Barnyardgrass (*Echinochloa crusgalli*) | Foxtail (*Setaria viridis*) | Crabgrass (*Digitaria adscendens*) | Johnson-grass | Soybean (*Glycine max*) | Cotton (*Gossypium indicum*) |
| Comp'd. No. | | | | | | | | |

TABLE 3-continued

| | Application rate of active ingredient (g ai/a) | Results of Upland Soil Treatment Test | | | | | | | |
|---|---|---|---|---|---|---|---|---|---|
| | | Herbicidal effects | | | | | | Crop injury | |
| | | Amaranth (Amaranthus viridis) | Common lamb-quarters | Barnyard-grass (Echinochloa crusgalli) | Foxtail (Setaria viridis) | Crabgrass (Digitaria adscendens) | Johnson-grass | Soybean (Glycine max) | Cotton (Gossypium indicum) |
| 1 | 50 | 100 | 100 | 100 | 100 | 100 | 100 | 0 | 0 |
| 2 | 50 | 80 | 85 | 80 | 85 | 80 | 100 | 0 | 0 |
| 3 | 50 | 100 | 100 | 100 | 100 | 100 | 100 | 0 | 0 |
| 4 | 50 | 100 | 100 | 100 | 100 | 100 | 100 | 0 | 0 |
| 5 | 50 | 100 | 100 | 100 | 100 | 100 | 100 | 0 | 0 |
| 6 | 50 | 95 | 90 | 95 | 100 | 85 | 100 | 0 | 0 |
| 7 | 50 | 80 | 85 | 85 | 90 | 80 | 100 | 0 | 0 |
| Comp. Comp'd | | | | | | | | | |
| A | 50 | 100 | 100 | 100 | 100 | 100 | 100 | 100 | 100 |
| B | 50 | 80 | 85 | 100 | 100 | 100 | 100 | 100 | 100 |
| C | 50 | 80 | 100 | 100 | 100 | 100 | 100 | 50 | 55 |
| D | 50 | 100 | 100 | 100 | 100 | 85 | 100 | 40 | 45 |
| E | 50 | 45 | 50 | 55 | 60 | 60 | 35 | 30 | 30 |

In Table 3 and Table 4 below, Compounds C, D and E indicate the following compounds, respectively.

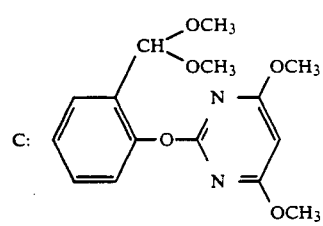

C:

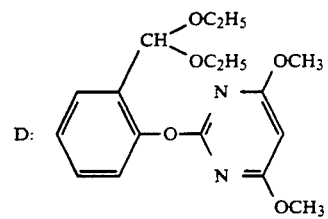

D:

(Compounds relating to the present application. They were each synthesized as comparative ones because they do not have selectivity although their activities are high.)

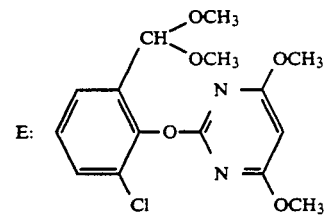

E:

(Compounds disclosed in Japanese Patent Laid-Open No. 115870/1988)

The results of the present test indicate that the compounds of the invention represented by the formula (I) exhibit high herbicidal effects against some broadleaf weeds and gramineous weeds including johnsongrass in soil treatment and can be used extremely safely for crops such as soybean and cotton compared with comparative compounds.

Test 3

Upland Foliar Application Test

Resin-made 1/1000-are pots were filled with the soil of an upland field. After they were fertilized, cotton and soybean were seeded and 3 cm soil covering was applied. Five days later, amaranth, common lambsquarters, barnyardgrass, green foxtail, large crabgrass and johnsongrass were seeded and 1 cm soil covering was applied. They were allowed to grow in a green house. When each plant grew to the stage of 2-3 leaves, an emulsion formulated from a predetermined amount of each test compound in a similar manner to the procedures described in Formulation Example 11 was diluted with water and then sprayed at a predetermined application rate by means of a pressure-operated sprayer. The application rate was controlled at 5 l per are. Influence to the crops and weeds were observed on the 40th day after the spray of the herbicides. The results are shown in Table 4 in which the degree of damages of each test plant and the degree of injury to each crop are shown in a similar manner to Test 2.

TABLE 4

| | Application rate of active ingredient (g ai/a) | Results of Upland Foliar Application Test | | | | | | | |
|---|---|---|---|---|---|---|---|---|---|
| | | Herbicidal effects | | | | | | Crop injury | |
| | | Amaranth (Amaranthus viridis) | Common lamb-quarters | Barnyard-grass (Echinochloa crusgalli) | Foxtail (Setaria viridis) | Crabgrass (Digitaria adscendens) | Johnson-grass | Soybean (Glycine max) | Cotton (Gossypium indicum) |
| Comp'd. No. | | | | | | | | | |
| 1 | 50 | 100 | 100 | 100 | 100 | 100 | 100 | 0 | 0 |
| 2 | 50 | 100 | 80 | 80 | 100 | 85 | 100 | 0 | 0 |
| 3 | 50 | 100 | 100 | 100 | 100 | 100 | 100 | 0 | 0 |
| 4 | 50 | 100 | 100 | 100 | 100 | 100 | 100 | 0 | 0 |

TABLE 4-continued

| | | Results of Upland Foliar Application Test | | | | | | | |
|---|---|---|---|---|---|---|---|---|---|
| | | Herbicidal effects | | | | | | Crop injury | |
| | Application rate of active ingredient (g ai/a) | Amaranth (*Amaranthus viridis*) | Common lamb-quarters | Barnyard-grass (*Echinochloa crusgalli*) | Foxtail (*Setaria viridis*) | Crabgrass (*Digitaria adscendens*) | Johnson-grass | Soybean (*Glycine max*) | Cotton (*Gossypium indicum*) |
| 5 | 50 | 100 | 100 | 100 | 100 | 100 | 100 | 0 | 0 |
| 6 | 50 | 95 | 90 | 95 | 95 | 90 | 100 | 0 | 0 |
| 7 | 50 | 90 | 85 | 95 | 90 | 90 | 100 | 0 | 0 |
| Comp. Comp'd | | | | | | | | | |
| A | 50 | 100 | 100 | 100 | 100 | 100 | 100 | 100 | 100 |
| B | 50 | 80 | 80 | 100 | 100 | 100 | 100 | 100 | 100 |
| C | 50 | 100 | 90 | 100 | 95 | 90 | 100 | 40 | 50 |
| D | 50 | 100 | 90 | 100 | 95 | 90 | 100 | 35 | 35 |
| E | 50 | 60 | 65 | 65 | 50 | 45 | 30 | 30 | 30 |

The results of the above test indicate that the compounds of the invention represented by the formula (I) exhibit high herbicidal effects against some broadleaf weeds and gramineous weeds including johnsongrass in foliage application and can be used extremely safely for crops such as soybean and cotton compared with the comparative compounds.

Test 4

Application Test on Johnsongrass Emerging from Rhizome

Resin-made 1/1000-are pots were filled with the soil of an upland field. After they were fertilized, rhizome of johnsongrass were transplanted to the pots and 3 cm soil covering was applied. They were allowed to grow in a green house. When each johnsongrass grew to the stage of 4-5 leaves, an emulsion formulated from a predetermined amount of each test compound in a similar manner to the procedures described in Formulation Example 11 was diluted with water and then sprayed at a predetermined application rate by means of a pressure-operated sprayer. The application rate was controlled at 5 l per are. The effect of each compound against the johnsongrass emerging from its rhizome was observed on the 50th day after the spray of the herbicides. The results are shown in Table 5 in which the herbicidal effect against johnsongrass is shown in a similar manner to Test 2.

TABLE 5

Foliar Application to Johnsongrass Emerging from Rhizome

| Compound | Application rate of active ingredient | Herbicidal effect against johnson-grass emerging from rhizome |
|---|---|---|
| Compound No. 1 | 20 | 100 |
| Compound No. 2 | 20 | 95 |
| Compound No. 3 | 20 | 100 |
| Compound No. 4 | 20 | 100 |
| Compound No. 5 | 20 | 100 |
| Compound No. 6 | 20 | 85 |
| Compound No. 7 | 20 | 80 |
| Comp. Comp'd A | 20 | 60 |
| Comp. Comp'd B | 20 | 35, |
| Comp. Comp'd C | 20 | 40 |
| Comp. Comp'd D | 20 | 50 |
| Comp. Comp'd E | 20 | 5 |

The results of the above test indicate that the compounds of the invention of the formula (1) exhibit the very high effect of controlling the johnsongrass emerging from rhizome.

Generally, the johnsongrass emerging from rhizome grows rapidly and have many buds. Therefore, if the durability of the herbicidal effect is insufficient, the johnsongrass can easily restore or re-emerge by consuming the herbicidal effect.

In contrast, since the compounds of the invention have the durable effect of inhibiting the growth of johnsongrass as shown in the results of the above test, they are very effective against the johnsongrass compared with the comparative compounds.

We claim:

1. A benzaldehyde acetal compound represented by the following formula (I):

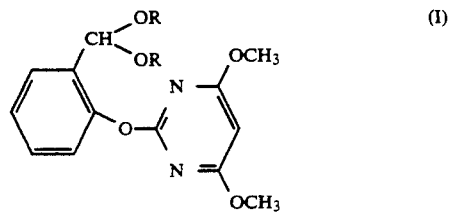

wherein R means a linear or branched $C_{3-8}$ alkyl group.

2. A herbicidal composition comprising as an active ingredient the benzaldehyde acetal compound (I) of claim 1.

3. A method of controlling weeds which comprises applying to an area susceptible to infestation with weeds a herbicidally effective amount of the compound (I) of claim 1.

4. The compound of claim 1, wherein R is straight chain.

5. The compound of claim 1, wherein R is —n—$C_3H_7$.

6. The compound of claim 1, wherein R is —n—$C_4H_9$.

7. The compound of claim 1, wherein R is —n—$C_5H_{11}$.

8. The compound of claim 1, wherein R is —n—$C_6H_{13}$.

9. The composition of claim 2, wherein R in compound (I) is straight chain.

10. The composition of claim 2, wherein R in compound (I) is —n—$C_3H_7$.

11. The composition of claim 2, wherein R in compound (I) is —n—$C_4H_9$.

12. The composition of claim 2, wherein R in compound (I) is —n—$C_5H_{11}$.

13. The composition of claim 2, wherein R in compound (I) is —n—$C_6H_{13}$.

14. The method of claim 3, wherein R in compound (I) is straight chain.

15. The method of claim 3, wherein R in compound (I) is —n—$C_3H_7$.

16. The method of claim 3, wherein R in compound (I) is —n—$C_4H_9$.

17. The method of claim 3, wherein R in compound (I) is —n—$C_5H_{11}$.

18. The method of claim 3, wherein R in compound (I) is —n—$C_6H_{13}$.

* * * * *